United States Patent [19]

Sahi

[11] Patent Number: 5,009,642
[45] Date of Patent: Apr. 23, 1991

[54] SELF-BLUNTING NEEDLE ASSEMBLY FOR USE WITH A CATHETER, AND CATHETER ASSEMBLY USING THE SAME

[75] Inventor: Carl R. Sahi, Coventry, Conn.
[73] Assignee: Bio-Plexus, Inc., Tolland, Conn.
[21] Appl. No.: 348,711
[22] Filed: May 8, 1989

Related U.S. Application Data

[63] Continuation-in-part of Ser. No. 101,610, Sep. 28, 1987, Pat. No. 4,828,547.

[51] Int. Cl.[5] .............................................. A61M 5/32
[52] U.S. Cl. .................................... 604/158; 604/110; 604/170
[58] Field of Search ....................... 604/110, 158–170

[56] References Cited

U.S. PATENT DOCUMENTS

| | | | |
|---|---|---|---|
| 3,923,066 | 12/1975 | Francisoud et al. | 604/170 |
| 4,274,408 | 6/1981 | Nimrod | 604/165 |
| 4,417,886 | 11/1983 | Frankhouser et al. | 604/164 |
| 4,525,157 | 6/1985 | Vaillancourt | 604/165 |
| 4,652,256 | 3/1987 | Vaillancourt | 604/164 |
| 4,772,264 | 9/1988 | Cragg | 604/158 |
| 4,828,547 | 5/1989 | Sahi et al. | 604/110 |
| 4,832,693 | 5/1989 | Gloyer | 604/110 |
| 4,832,696 | 5/1989 | Luther et al. | 604/110 |
| 4,863,431 | 9/1989 | Vaillancourt | 604/168 |
| 4,869,717 | 9/1989 | Adair | 604/164 |

Primary Examiner—Stephen C. Pellegrino
Assistant Examiner—Ralph A. Lewis

[57] ABSTRACT

A self-blunting needle assembly (10) for use with a catheter (40), and a catheter assembly (50) attained by mounting the self-blunting needle assembly into a catheter are disclosed. The needle (12) includes a needle shaft (14) having a connector (18) thereon and a blunting device (28) including an elongate probe (30) having a retainer (32) thereon. The connector (18) engages the retainer (32) to provide a lost motion connection between the blunting device (28) and the needle (12). The needle assembly (10) is mounted within a catheter (40) by a force fit of the retainer into the hub chamber (42a) of the catheter, with the needle puncture tip (16) protruding beyond the catheter tube tip (46). After injection of the catheter by means of the needle into a patient's vein, manual withdrawal of the needle from the catheter initially shifts the needle relative to the blunting device (28) by virtue of the lost motion connector, thereby causing the elongate probe (30) to extend beyond the needle tip (16) and blunt the needle. Continued withdrawal removes the needle assembly from the catheter.

12 Claims, 2 Drawing Sheets

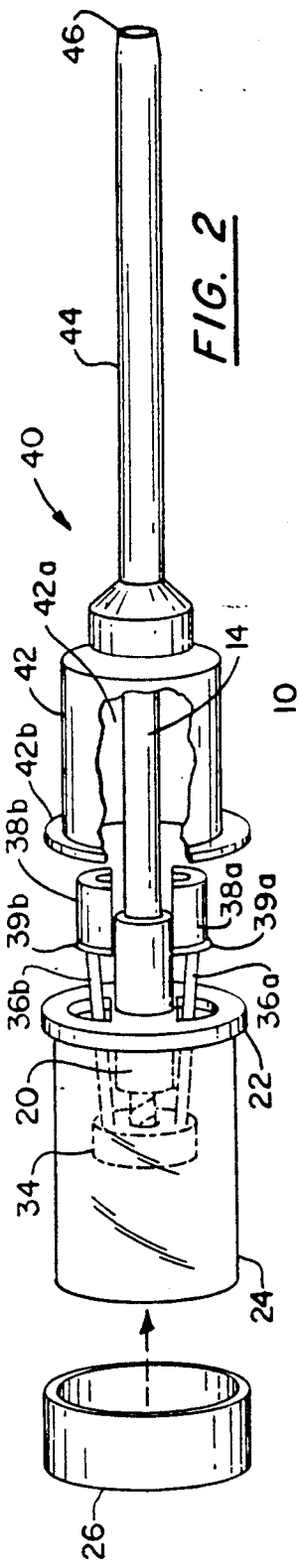
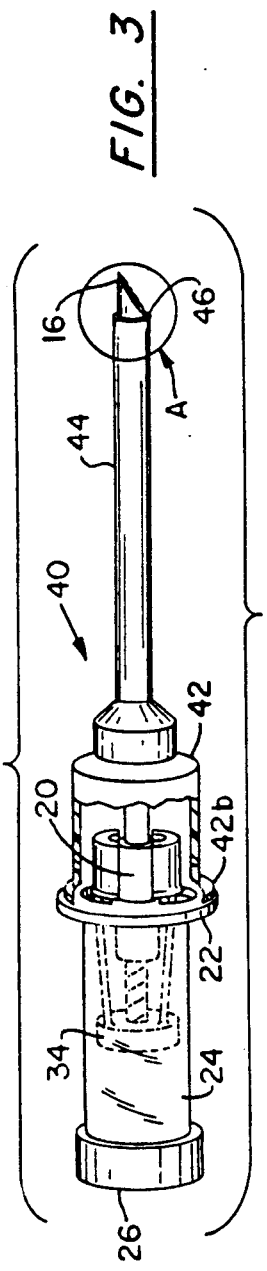
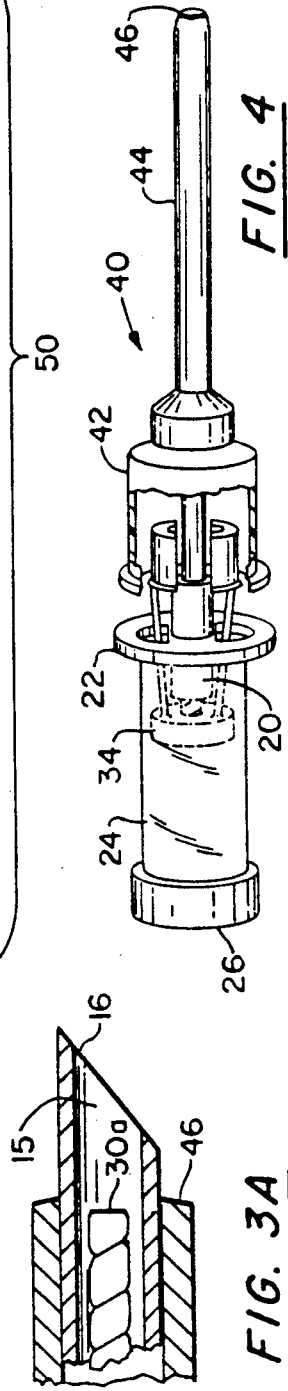
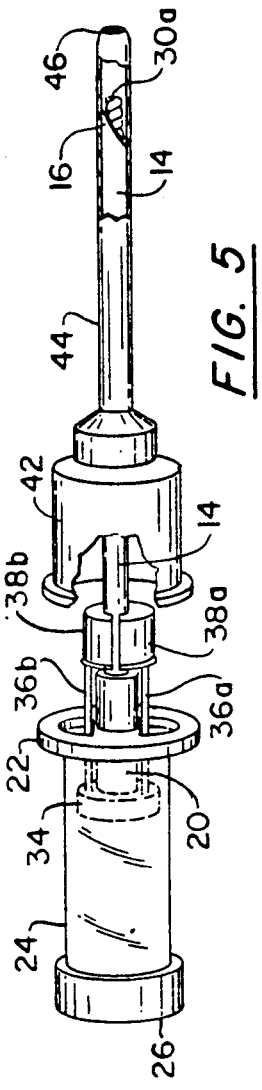
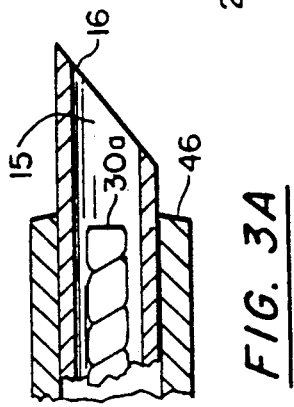

SELF-BLUNTING NEEDLE ASSEMBLY FOR USE WITH A CATHETER, AND CATHETER ASSEMBLY USING THE SAME

CROSS-REFERENCE TO RELATED APPLICATION

This application is a continuation-in-part of copending patent application Ser. No. 07/101,610, filed on Sept. 28, 1987 in the name of Carl R. Sahi, et al and entitled "SELF-BLUNTING NEEDLE ASSEMBLY AND DEVICE INCLUDING THE SAME", now U.S. Pat. No. 4,828,547.

BACKGROUND OF THE INVENTION

1. Field Of The Invention

The present invention is concerned with a self-blunting needle assembly especially suited for use in conjunction with a catheter, and with catheter assemblies including such needle assemblies. More particularly, the present invention is concerned with a needle assembly which is self-blunted prior to removal from an over-the-needle catheter implanted by use of the needle assembly.

2. Description of Related Art

A. Hypodermic Syringes Employing Locking Means Or The Like

Hypodermic syringes including locking means or the like designed to prevent reuse of the device are known. For example, U.S. Pat. No. 4,367,738 discloses a hypodermic syringe in which the plunger rod is fitted with flexible spikes which expand as the plunger is depressed in order to lock the plunger rod within the barrel portion of the syringe, thereby preventing retraction of the plunger rod for reuse of the syringe.

U.S. Pat. No. 3,478,937 discloses a syringe in which a collar unit on the plunger stem serves to prevent subsequent retraction of the plunger for reuse of the device.

U.S. Pat. No. 4,233,975 discloses a syringe in which a plug is seated by movement of the plunger rod and blocks further liquid flow to the needle mouth.

U.S. Pat. No. 4,391,273 discloses a syringe in which the plunger carries a protruding pin 67 which punctures a lower wall of the barrel in order to prevent reuse of the syringe.

U.S. Pat. No. 1,654,905 discloses a measuring syringe in which a tapering needle 9 meters the amount of discharge from the device, as explained beginning at page 1, line 72 of the patent.

B. Hypodermic Syringes With Means to Prevent Accidental Stick-Wounds

The art also shows syringes which are equipped with means intended to prevent accidental sticking of persons, such as the operator, with the needle. It is estimated that over 2,000 accidental needle-stick wounds are sustained by health care workers in the United States each day. The problem is aggravated by the trend of moving treatment out of hospitals and into doctors' offices and neighborhood clinics as part of a program to reduce health care costs. This trend increases the number and dispersion of health care workers who administer injections and draw blood samples, while reducing the frequency of such injections per individual health care worker. As a consequence, a larger number of less experienced people are administering injections and/or taking blood samples. Although in the past an occasional serious illness such as that caused by the hepatitis B virus was sustained as a result of an accidental needle-stick wound, the problem was not considered to be a serious one until the advent of the spreading of human immunodeficiency virus (HIV) infection and the knowledge that this virus is transmissible to health care workers through needle-stick wounds from a contaminated needle. The HIV causes acquired immune deficiency syndrome (AIDS), a disease which, insofar as is presently known, is invariably fatal and which has already killed tens of thousands and infected possibly millions more. HIV is often referred to simply as "the AIDS virus" and the Surgeon General of the United States of America noted in a published (September, 1987) interview that there is no better way to become infected with the AIDS virus than to take blood from an AIDS patient and accidentally inflict a needle-stick wound with the contaminated needle. This serious situation has stimulated activity to develop devices which reduce or eliminate the possibility of accidental needle-stick wounds without excessively increasing the unit cost of needles.

U.S. Pat. No. 3,890,971 discloses a single use, safety syringe which includes a plunger which is permanently lockable by detent members when the plunger has been operated to expel liquid from the barrel portion of the syringe. The disclosed structure further includes a slidable needle cap which is also permanently lockable by detent members to encase the needle within the sleeve.

U.S. Pat. No. 4,810,248 discloses a hypodermic syringe in which a combination safety sheath and needle cap is slidably mounted on the barrel to extend between a retracted position and an extended position. Means to lock the sheath in the extended position are also provided, as illustrated in the Figures of the drawing, to shield the needle to prevent inadvertent needle sticks.

U.S. Pat. No. 4,808,169 discloses a hypodermic syringe in which a double-ended hypodermic needle cannula is retained between a pair of rotatable jaws. A piston is movable through the cartridge of the syringe for expulsing the fluid contents through the needle cannula and for engaging the cannula to retrieve it irretrievably into the cartridge, to render the syringe nonreusable and protect against accidental stick wounds.

U.S. Pat. No. 4,801,295 discloses a hypodermic syringe including a sheath which is movably mounted on the syringe barrel to an extended position to cover and protect the needle. A second position of the sheath relative to the barrel and needle results in at least partially exposing the needle for use, and a third position of the sheath is employed to cover the needle with the sheath for disposal of the device. Means are provided to irreversibly lock the sheath in the third position to prevent misuse of the device.

Brochures distributed by ICU Medical Inc., of Mission Viejo, California, show a hypodermic syringe which has a sheath carried on the needle. Insofar as can be discerned from the brochure, which contains the notation "Patent Pending", the needle extends beyond the sheath for use, and the sheath is grasped by the operator upon withdrawing the needle in order to retract the needle within the sheath upon withdrawal of the needle from the patient. In this way, the sheath guards against accidental pricking of the operator with the withdrawn needle.

C. Catheter-Needle Assemblies

The use of syringe needle assemblies to insert catheters is of course well known in the art, as exemplified by U.S. Pat. No. 4,529,399. This device uses a needle member having a bore within which a catheter tube is carried, the needle being constructed to be dismantled and withdrawn to leave the catheter remaining in place, as illustrated in the drawings of the patent.

U.S. Pat. No. 4,274,408 discloses a means for inserting a catheter guide wire (12) into the vein of a patient by use of a hypodermic needle syringe. The patent discloses a locking means provided by the clip 16 (shown in FIGS. 1 and 7) which is designed to retain the guide wire 12 against any longitudinal movement relative to the syringe. After injection of the needle shaft into the vein, clip 16 is removed in order to permit withdrawal of the syringe back over the guide wire 12, as explained at column 3, lines 57–65 and column 4, lines 60–63 of the patent. The guide wire is then employed to guide a catheter 68 (FIG. 11) into the vein by means of the implanted guide wire, as explained starting at column 5, lines 4–9.

SUMMARY OF THE INVENTION

In accordance with a specific aspect of the present invention, there is provided a catheter assembly comprising the following components. One component is a catheter having a hub, within which is formed a hub chamber, and a catheter tube extending from the hub and terminating in a tube tip, the tube having a tube bore which extends therethrough. Another component is a needle assembly carried by the catheter, the needle assembly comprising a needle member in which is mounted a blunting member. The needle member is comprised of a needle shaft having a needle bore extending therethrough, the needle shaft terminating at one end in a puncture tip and having an opposite, proximal end on which is carried a connector means. The blunting member comprises an elongate probe having a retainer means carried thereon, the probe being slidably mounted within the needle bore with the retainer means carried exteriorly of the needle bore and in engagement with the connector means. The needle member is axially movable relative to the blunting member, from a retracted condition of the blunting member, in which the probe is short of the puncture tip of the needle member, to an extended condition of the blunting member, in which the probe protrudes outwardly of, and thereby blunts, the puncture tip. The retainer means is force-fit within the hub chamber to hold the needle assembly in place within the catheter and so positioned that (1) the needle shaft is disposed within the tube bore with the puncture tip thereof extending outwardly of the tube tip, and (2) the needle member is accessible from exteriorly of the catheter at the hub. The retainer means and the connector means are dimensioned and configured to provide a lost motion connection between the needle member and the blunting member, whereby an initial stage of withdrawal of the needle member from the catheter moves the needle member relative to the blunting member to change the blunting member from its retracted condition to its extended condition, thereby blunting the puncture tip. Continued withdrawal of the needle member beyond the initial stage overcomes the force-fit between the retainer means and the hub chamber, and extracts the needle assembly from the catheter.

Another aspect of the present invention provides a self-blunting needle assembly as a separate article, well suited for use with readily available over-the-needle catheters, for example, with catheters having a hub within which is formed a hub chamber, and a catheter tube extending from the hub and terminating in a tube tip, the tube having a tube bore extending therethrough. The needle assembly of the present invention is one as described above in combination with a catheter.

In one aspect of the present invention, the connector means comprises a ferrule slide and the retaining means comprises a clamping member which imposes a pressure grip on the ferrule slide, whereby the lost motion of the initial stage of withdrawal of the needle member is attained by overcoming the pressure grip to slide the ferrule slide through the clamping member.

In another aspect of the present invention, the retaining means further comprises resilient means biasing the clamping member towards engagement with the needle shaft, the ferrule slide resisting the resilient means and urging the clamping member into force-fit engagement with the hub chamber whereby, upon the ferrule slide clearing the clamping member, the clamping member is freed to move towards gripping engagement with the needle shaft.

Yet another aspect of the present invention provides retainer means which further comprise an end stop affixed to the needle shaft, and resilient means comprising one or more resilient leg members carrying the clamping means axially spaced from the end stop whereby, upon the ferrule slide clearing the clamping means, the ferrule slide is trapped between the end stop and the clamping means thereby preventing further relative movement between the needle member and the blunting member.

Yet another aspect of the present invention provides for the retainer means to comprise at least two resilient legs affixed at one end to the needle shaft and having opposite, distal ends, and the clamping means to comprise gripping pads disposed at the distal ends of the resilient legs. In this aspect of the invention, the clamping means may have inner gripping surfaces dimensioned and configured to grip the ferrule slide, and outer gripping surfaces dimensioned and configured to grip the hub chamber in force-fit engagement therewith. In a related aspect of the present invention, the connector members, the retainer means and the hub chamber are each dimensioned and configured to cooperate with each other to provide a stronger engagement force between the retainer means and the hub chamber than between the retainer means and the connector means. In a specific embodiment of the present invention, the clamping means may comprise split segments of a ring and the ferrule slide may be of cylindrical configuration.

Other aspects of the invention are set forth in the drawings and in the detailed description given below.

BRIEF DESCRIPTION OF THE DRAWINGS

FIG. 2 is a perspective view with parts broken away of an incompletely assembled catheter assembly including the needle assembly of FIG. 1;

FIG. 3 is a perspective view with parts broken away and on a scale which is reduced relative to FIG. 2, of the completely assembled catheter assembly of FIG. 2;

FIG. 3A is a cross-sectional view of the portion of FIG. 3 enclosed by the circle A and on a scale which is enlarged relative to FIG. 3;

FIG. 4 is a view corresponding to that of FIG. 3, showing an initial stage of withdrawal of the needle assembly from the catheter; and FIG. 5 is a view corresponding to that of FIG. 4, showing a later stage of the withdrawal of the needle assembly from the catheter.

DETAILED DESCRIPTION OF THE INVENTION AND PREFERRED EMBODIMENTS THEREOF

Figures 1, 1A:
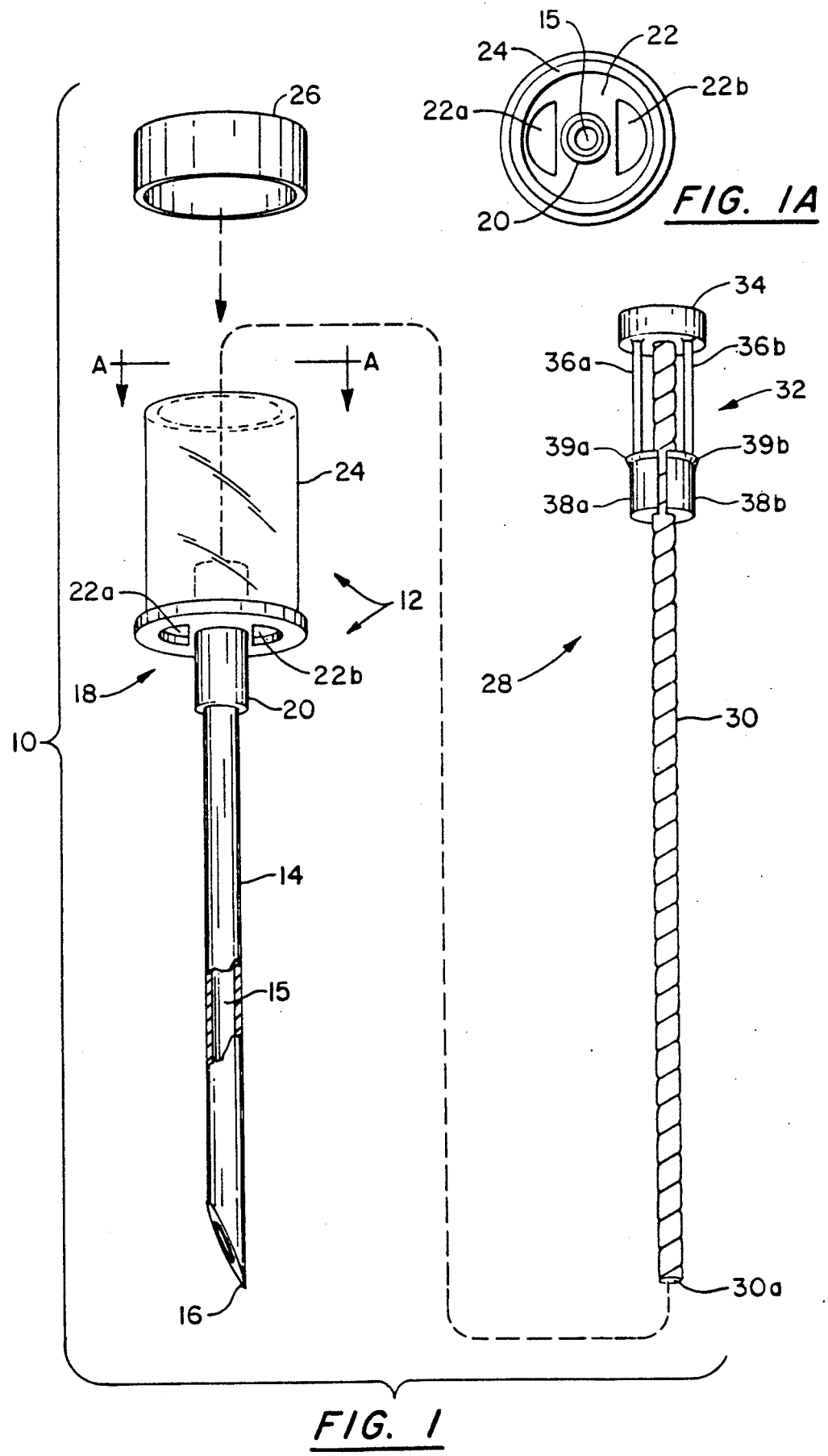
FIG. 1 is a perspective, exploded view of a needle member and a blunting member comprising one embodiment of a needle assembly of the present invention.
FIG. 1A is a view taken generally along line A—A of FIG. 1, perpendicularly to the longitudinal axis of the needle member of FIG. 1.

Patent Application Ser. No. 07/101,610, the parent of this application, discloses a self-blunting needle assembly in which an elongate probe member is carried within the bore of the shank of a needle, in an assembly which includes transfer means to move the blunting member from its retracted position, in which the probe is short of the puncture tip of the needle, to its extended position in which the probe protrudes outwardly of, and thereby blunts, the puncture tip. The transfer means may comprise, for example, a piston disposed in the fluid flow stream of the needle so that the flow of fluid advances the blunting member to its extended position. Alternatively, the transfer means may comprise a member to transmit mechanical force to the blunting member, for example, an extension member or the like, which is driven by the plunger of a hypodermic syringe to advance the blunting member. The needle assembly also includes a locking means dimensioned and configured to engage the blunting member and retain it in its extended position after use of the needle. In this matter, upon withdrawal of the needle from the patient or a connecting device, the tip is blunted and accidental stick wounds are prevented.

Referring now to the drawings, there is shown in the exploded view of FIG. 1 a needle assembly which is particularly well adapted for use in implanting over-the-needle catheters. As indicated above, such catheters are well known and essentially comprise a catheter fitted over the shank of a hypodermic-type needle, the puncture tip of the needle protruding beyond the tip of the catheter. The needle is injected into the patient to penetrate into a vein, the needle carrying the tube tip of the catheter tube into the vein. The catheter is then secured in place by any convenient means, and the needle is withdrawn from it to leave behind the implanted catheter which may then be connected to a fluid source or otherwise employed in the known manner.

FIG. 1 shows an exploded, somewhat schematic perspective view of a needle assembly 10 comprised of a needle member 12 and a blunting member 28. Needle member 12 comprises a needle shaft 14 which terminates in a puncture tip 16 at one end and having at its opposite, proximal end a connector means 18. A portion of needle shaft 14 is broken away to show needle bore 15 which extends therethrough, terminating in a suitable opening (unnumbered) in puncture tip 16 and another suitable opening (unnumbered) at the opposite, proximal end of needle shank 14; the latter opening is visible in FIG. 1A. In the illustrated embodiment, connector means 18 is comprised of a ferrule slide 20 affixed over the proximal end of needle shaft 14 and surmounted by a disk-shaped collar 22 which has a pair of semi-circular shaped cutouts 22a, 22b extending therethrough. Collar 22 surmounts ferrule slide 20 at an intermediate point thereof, so that a portion of ferrule slide 20 projects into a cylindrical collection tube 24 which is affixed to collar 22 coaxially with needle shaft 14. As shown in FIG. 1A, ferrule slide 20 is of tube-like construction, that is, it is opened at each end, so as to place needle bore 15 in flow communication between the opening in puncture tip 16 and the interior of collection tube 24.

Collection tube 24 is open at both ends thereof, may be made of any suitable material and is desirably transparent, for example, it may be made of glass or a transparent plastic, i.e., a transparent synthetic organic polymeric material. Collection tube 24 is affixed to collar 22 in liquid-tight fashion by any suitable means, such as a suitable adhesive or by ultrasonic welding or the like. This closes one end of collection tube 24, except for cut-outs 22a and 22b. A closure cap 26 fits over the remaining open end of collection tube 24, i.e., the end opposite that which is affixed to collar 22, and is affixed by any suitable means to collection tube 24 after blunting member 28 has been inserted through the open end of collection tube 24, as described below.

Blunting member 28 comprises an elongate probe 30 which, in the illustrated embodiment, is striated by means of a helical groove formed therein. Elongate probe 30 could be formed with axially extending grooves or striations formed in the surface thereof, or could be made with a smooth exterior surface, and could be employed either in the form of a hollow tube or a solid rod-like structure. In any case, probe 30 has a retainer means 32 mounted thereon. In the illustrated embodiment, the retainer means 32 comprises an end stop 34 which is affixed at one end of probe 30 and is generally of disk-shaped configuration. End stop 34 includes resilient means provided, in this case, by a pair of resilient legs 36a, 36b which extend from end stop 34 towards the distal end 30a of elongate probe 30. Resilient legs 36a, 36b terminate at their respective distal ends in respective clamping means provided, in this case, by split ring sections 38a, 38b. Split ring sections 38a, 38b each has a small circumferential flange, 39a and 39b respectively (FIG. 1) formed on the sides thereof adjacent to legs 36a, 36b. Flanges 39a, 39b are tapered to flare outwardly in the direction towards end stop 34 for a purpose described below. Resilient legs 36a and 36b are constructed of a resilient material so that if spread apart, i.e., if spread in an axially outward direction relative to the longitudinal axis of probe 30, the legs will tend to spring back to the position illustrated in FIG. 1.

Blunting member 28 and needle member 12 are assembled by, prior to securing closure cap 26 in place, inserting the distal end 30a of elongate probe 30 into needle bore 15 through the proximal end of needle shaft 14 (the end to which slide ferrule 20 is secured), as indicated by the dash-line arrow of FIG. 1. Resilient legs 36a and 36b are spread sufficiently to permit split ring sections 38a and 38b and then legs 36a, 36b to pass through, respectively, cut-outs 22a, 22b in collar 22 in the manner illustrated in FIG. 2, which shows resilient legs 36a, 36b still slightly spread apart for passage through cut-outs 22a, 22b. The split ring sections 38a and 38b have a profile which substantially conforms to that of cut-outs 22a and 22b and are otherwise dimensioned and configured to be a tight fit in passing through cut-outs 22a and 22b. Flanges 39a and 39b are preferably somewhat flexible and are flared as described above to permit passage of split ring sections 38a and 38b through cut-outs 22a, 22b in the direction towards puncture tip 16, but to prevent or make much more difficult passage in the opposite direction through the cut-outs 22a, 22b. Although not shown in the drawings, the end of the ferrule slide 20 facing away from the puncture tip 16 of the needle may taper inwardly in the direction away from the puncture tip, to facilitate centering of split ring sections 38a, 38b on the ferrule slide, and passage thereover during assembly. After passing through cut-outs 22a, 22b, resilient legs 36a, 38b are released and will close so that split ring sections 38a, 38b will engage and grip between them the right-hand portion (as viewed in FIGS. 2-5) of slide ferrule 20. Closure cap 26 is then affixed to the open end of collection tube 24 to complete the assembly of needle member 12 and blunting member 28 to provide a needle assembly 10 (FIGS. 1 and 3). The needle assembly is then inserted into a suitable catheter to provide a catheter assembly 50. For economy of illustration, even though FIG. 2 shows the assembly of needle assembly 10 to be not quite complete, the needle assembly is shown partially inserted into a catheter 40 which is comprised of a hub 42 and a catheter tube 44 which terminates in a tube tip 46. A portion of catheter tube 44 is broken away in FIG. 2 to illustrate tube bore 48 through which needle shaft 14 (within which is carried elongate probe 30) is being inserted. A hub chamber 42a is formed within hub 42 and is in flow communication with tube bore 48.

FIG. 3 shows the needle assembly 10 properly positioned within catheter 40 to provide catheter assembly 50, in which puncture tip 16 protrudes outwardly of tube tip 46 of catheter 40 and collar 22 abuts against the rim 42b of hub 42. Slide ferrule 20 is seen to be forced between split ring sections 38a, 38b thereby forcing them radially outwardly and into gripping engagement with the interior walls (unnumbered) of hub chamber 42a. The needle member 12 and the blunting member 28 are each dimensioned and configured so that when they are assembled as described above, the distal tip 30a of elongate probe 30 will be in its retracted condition as shown in FIG. 3A, in which tip 30a is short of puncture tip 16, i.e., does not protrude from the opening at puncture tip 16, thereby preventing any interference by probe 30 with normal utilization of needle member 12. It will be noted that the length of elongate probe 30 is such that end stop 34 is spaced an axial distance from the adjacent end (unnumbered) of ferrule slide 20; this spacing provides a distance for travel of ferrule slide 20 towards end stop 34 upon the initial stage of withdrawal of needle assembly 10 as described below, before imposing movement upon blunting member 28. Thus, a lost motion connection is formed between blunting member 28 and needle member 12.

In use, the catheter assembly 50 of FIG. 3 is injected into a patient so that puncture tip 16 enters into a vein, thereby carrying tube tip 46 within the vein in the conventional manner of use of an over-the-needle catheter. When needle tip 16 enters the vein, the patient's blood pressure will force blood through needle bore 15, in the annular space formed between elongate probe 30 and the interior walls of needle bore 15. Linear or spiral striations formed in elongate probe 30 facilitate such blood flow. Alternatively, elongate probe 30 may be of hollow construction so that the blood will flow therethrough. As noted above, elongate probe 30 may be hollow, in which case the bore of elongate probe 30 will be in flow communication with a central opening (not shown in the drawings) in end stop 34, through which the blood flows into collection tube 24. If elongate probe 30 is not hollow, a plurality of smaller opening (not shown in the drawings) which may be arcuate in shape, will be formed in end stop 34 in axial alignment with the annular space between elongate probe 30, to admit the blood flow into collection tube 24. Suitable seals (not shown in the drawings) may be used to prevent blood (or other body fluids) from flowing through the cut-outs 22a and 22b and leaking from the device. In any case, the blood flows through needle bore 15 thence into collection tube 24, providing an indication to the operator that a vein has been satisfactorily struck. The catheter 40 may then be secured in place by any conventional means, such as by taping it to the patient. The operator may grasp hub 42 between thumb and forefinger of one hand while grasping collection tube 24 between thumb and forefinger of the other hand and pulling it, and thereby needle assembly 50 leftwardly as viewed in the drawings, relative to catheter 40. Alternatively, for one-handed operation, collection tube 24 may be grasped between the thumb and middle finger and the forefinger used to push the needle assembly away from hub 42. In any case, because of the above-described lost motion connection, slide ferrule 20 will be moved leftwardly along with the rest of needle member 12, but blunting member 28 will remain in place, the resultant relative movement changing blunting member 28 from its retracted position (illustrated in FIG. 3A) to its extended position (illustrated in FIG. 5) in which distal tip 30a of elongate probe 30 projects beyond, and thereby blunts, puncture tip 16 of needle shaft 14. As needle member 12 continues to be withdrawn leftwardly during the initial stage of withdrawal of needle assembly 10 from catheter 40, slide ferrule 22 escapes from between opposed split ring sections 38a, 38b at about the time the leftward (as viewed in FIGS. 2-5) end of slide ferrule 22 engages end stop 34. The resiliency of resilient legs 36a, 36b causes them to return to the closed position illustrated in FIG. 1 and close towards or upon needle shaft 14, as illustrated in FIG. 5. Slide ferrule 20 is seen to be thereby trapped between end stop 34 and closed split ring sections 38a, 38b, thereby locking needle member 12 and blunting member 28 together to prevent any further relative movement between them. In this manner, elongate probe 30 of blunting member 28 is locked in its extended position, effectively blunting puncture tip 16 prior to complete withdrawal of it from catheter 40, thereby preventing accidental stick wounds in case the operator should accidentally stick himself or herself with the needle. Continued withdrawal leftwardly (as viewed in FIG. 5) of collection tube 24 serves to withdraw the needle assembly 10 (comprised of interconnected needle member 12 and blunting member 28) as a unit from catheter 40. Upon such removal of needle assembly 10, catheter 40 may be used in the normal manner, as by being connected by means of hub 42 in liquid flow communication to a source of liquid.

The gripping or engagement force between the retainer means (32) and the hub chamber (42a) (e.g., between split ring segments 38a, 38b and the walls of hub chamber 42a) is greater than the gripping or engagement force between the retainer means (32) and the connector means (e.g., between split ring segments 38a, 38b and slide ferrule 20). This assures that the needle member (12) moves relative to the blunting member (28) before the needle assembly (10) is withdrawn as a unit out of the catheter (40). In the illustrated embodiment of the invention, flanges 39a, 39b also help to increase the frictional resistance between hub chamber 42a and the exterior surfaces (unnumbered) of split ring sections 38a, 38b. In addition, the exterior surfaces of split ring sections 38a, 38b and/or the walls of hub chamber 42a may be textured or otherwise treated, or the materials from which one or both are made are selected, to increase frictional engagement therebetween. Alternatively, or in addition, the frictional resistance to sliding between the surface of slide ferrule 20 and the interior surfaces of split ring sections 38a, 38b may be reduced by suitably treating or configuring one or both of those surfaces, e.g., by applying a suitable lubricant, such as a silicone lubricant, to them, or by suitably selecting the materials from which they are made.

Tests with conventional hypodermic syringe needles have shown that even when utilizing a rod-like (no bore) elongate probe and flowing a liquid in the annular space between the elongate probe and the inside walls of the needle bore, an adequate delivery rate of liquid (e.g., blood from the patient's vein) may be attained. For example, stock hypodermic tubing used for the needle shaft made of T304/T316 stainless steel is commercially available in a wide range of gauges. An 18RW gauge steel hypodermic tubing has a nominal inside diameter of 0.033 inches. The manufacturer's specifications (All-Tube Division, a Microgroup Company, of Midway, Massachusetts) call for an inside diameter range of 0.0315 to 0.0345 inches. A solid elongate probe of the type illustrated in the drawings may be made from a wire stock which preferably has striations or flutings thereon and may have a diameter of, e.g., about 0.020 to 0.028 inches. This type of stock will provide a satisfactory self-blunting probe when used in combination with an 18RW hypodermic tubing, allowing blood flow through the needle member to the collection tube 24, in order to provide an indication that a vein has been struck. A satisfactorily strong needle shank can also be made from 18XX gauge stainless steel stock hypodermic tubing, which has a nominal inside diameter of 0.045 inches, the manufacturer's specifications calling for an inside diameter range of from 0.044 to 0.046 inches. Within this stock tubing a hollow probe made of 19XX gauge stock hypodermic tubing, which has a nominal outside diameter of 0.0425 inches, and a specification range of from 0.042 to 0.043 inches, may be utilized. The 19XX gauge stock tubing has a nominal inside diameter of 0.0375 inches, the specifications calling for an inside diameter range of from 0.0365 to 0.0385 inches. Thus, a hollow tube probe made of 19XX gauge stock hypodermic tubing will slidably fit within a needle shank made of 18XX gauge hypodermic tubing and provide a probe bore through which blood (or other bodily fluid) may be flowed of from 0.0365 to 0.0385 inches diameter. This is larger than the inside diameter of an unencumbered 18RW gauge needle.

While a specific embodiment of the invention has been described with particular reference to a self-blunting needle assembly used for injection of an over-the-needle catheter directly into the body, those skilled in the art will appreciate that the invention is not necessarily so limited but, rather, is broadly applicable to provide self-blunting needle assemblies designed for removal from a device which is implanted, or connected to another device, by being carried on the needle assembly. For example, connecting a needle-mounted connector to any intravenous (IV) device by inserting the needle through a membrane seal of such IV-connecting device, of course exposes the needle to the fluids being transported through the IV-connecting device. Upon breaking the connection by removing the needle, an accidental needle stick wound can transmit infection from the needle, even though the needle was never directly injected into the patient's body because it nonetheless was contacted by the patient's body fluids or other contaminated fluids.

Generally, the self-blunting action of the elongate probe in its extended condition or position has been found to be effective to prevent accidental stick-wounds even when the probe protrudes a very small distance, as little as about five one-thousandths (0.005) to ten one-thousandths (0.010) of an inch, beyond the most distal portion of the puncture tip. Accordingly, in most if not all cases, no patient discomfort or harm will be sustained by having the probe in its extended, self-blunting position even while the needle is still within the patient's body or vein. In fact, the elongate probe could extend as much as fifty one-thousandths of an inch (0.050) or more beyond the most distal portion of the puncture tip, without discomfort or danger to the patient. Nonetheless, the present invention permits deferring movement of the probe to its extended position not only until after the needle is injected, but until after it is withdrawn from the patient and retracted to within the catheter tube. However, the blunting probe is placed in its extended, blunting position prior to removal of the needle from the catheter tube, thereby preventing accidental stick wounds to the operator.

Needle assemblies and catheter assemblies of the invention have broad utility for medical, veterinary and other uses, including autopsies and preparation of bodies for interment. Generally, the assemblies of the present invention are useful whenever a needle must be injected into tissue or into a connector or other device, in which the needle and/or its tip is exposed to contamination, and it is desired to blunt the needle to prevent reuse and accidental sticking by it.

While the invention has been described in detail with reference to specific preferred embodiments thereof, it will be appreciated that such specific embodiments are illustrative only and the scope of the invention is more fully described in the appended claims.

What is claimed is:

1. A catheter assembly comprising:
   (a) a catheter having a hub within which is formed a hub chamber, and a catheter tube extending from the hub and terminating in a tube tip, the tube having a tube bore extending therethrough;
   (b) a needle assembly carried by the catheter and comprising a needle member in which is mounted a blunting member,
      (i) the needle member comprising a needle shaft having a needle bore extending therethrough, the needle shaft terminating at one end in a puncture tip and having an opposite, proximal end on which is carried a connector means,
      (ii) the blunting member comprising an elongate probe having a retainer means carried thereon, the probe being slidably mounted within the needle bore with the retainer means carried exteriorly of the needle bore and the connector means and in engagement with the connector means,
      (iii) the needle member being axially movable relative to the blunting member, from a retracted condition of the blunting member, in which the probe is short of the puncture tip of the needle member, to an extended condition of the blunting member, in which the probe protrudes outwardly of, and thereby blunts, the puncture tip; the retainer means being force-fit within the hub chamber to hold the needle assembly in place within the catheter and so positioned that (1) the needle shaft is disposed within the tube bore with the puncture tip thereof extending outwardly of the tube tip, and (2) the needle member is accessible from exteriorly of the catheter at the hub; the retainer means and the connector means being dimensioned and configured to provide a lost motion connection between the needle member and the blunting member, whereby an initial stage of withdrawal of the needle member from the catheter moves the needle member relative to the blunting member to change the blunting member from its retracted condition to its extended condition, thereby blunting the puncture tip, and continued withdrawal of the needle member beyond the initial stage overcomes the force-fit between the retainer means and the hub chamber and extracts the needle assembly from the catheter, wherein the connector means comprises a ferrule slide and the retaining means comprises a clamping member which imposes a pressure grip on the ferrule slide, whereby the lost motion is attained by overcoming the pressure grip to slide the ferrule slide through the clamping member.

2. A self-blunting needle assembly for use with a catheter having a hub within which is formed a hub chamber, and a catheter tube extending from the hub and terminating in a tube tip, the tube having a tube bore extending therethrough, the needle assembly comprising:
  (a) a needle member in which is mounted a blunting member,
    (i) the needle member comprising a needle shaft having a needle bore extending therethrough, the needle shaft terminating at one end in a puncture tip and having an opposite, proximal end on which is carried a connector means,
    (ii) the blunting member comprising an elongate probe having a retainer means carried thereon, the probe being slidably mounted within the needle bore with the retainer means carried exteriorly of the needle bore and in engagement with the connector means,
    (iii) the needle member being axially movable relative to the blunting member, from a retracted condition of the blunting member, in which the probe is short of the puncture tip, to an extended condition of the blunting member, in which the probe protrudes outwardly of, and thereby blunts, the puncture tip of the needle member;
  the retainer means being dimensioned and configured to be force-fit within the hub chamber of a catheter to hold the needle assembly in place within such catheter and so positioned that (1) the needle shaft would be disposed within the tube bore of such catheter with the puncture tip thereof extending outwardly of the tube tip of such catheter, and (2) the needle member would be accessible from exteriorly of such catheter at the hub thereof; the retainer means and the connector means being dimensioned and configured to provide a lost motion connection between the needle member and the blunting member, whereby an initial stage of withdrawal of the needle member from such catheter moves the needle member relative to the blunting member to change the blunting member from its retracted condition to its extended condition, thereby blunting the needle, and continued withdrawal of the needle member beyond the initial stage overcomes the force-fit between the retainer means and the hub chamber of such catheter and extracts the needle assembly from such catheter, wherein the connector means comprises a ferrule slide and the retaining means comprises a clamping member which imposes a pressure grip on the ferrule slide, whereby the lost motion is attained by overcoming the pressure grip to slide the ferrule slide through the clamping member.

3. The assembly of claim 1 or claim 2 wherein the retaining means further comprises resilient means biasing the clamping member towards engagement with the needle shaft, the ferrule slide resisting the resilient means and urging the clamping member into force-fit engagement with the hub chamber whereby, upon the ferrule slide clearing the clamping member, the clamping member is freed to move towards gripping engagement with the needle shaft.

4. The assembly of claim 3 wherein the retainer means further comprises an end stop affixed to the needle shaft and the resilient means comprises one or more resilient leg members carrying the clamping means axially spaced from the end stop whereby, upon the ferrule slide clearing the clamping means, the ferrule slide is trapped between the end stop and the clamping means thereby preventing further relative movement between the needle member and the blunting member.

5. The assembly of claim 4 wherein the retainer means comprises at least two resilient legs affixed at one end to the needle shaft and having opposite, distal ends, and the clamping means comprises gripping pads disposed at the distal ends of the resilient legs.

6. The assembly of claim 5 wherein the clamping means have inner gripping surfaces dimensioned and configured to grip the ferrule slide, and outer gripping surfaces dimensioned and configured to grip the hub chamber in force-fit engagement therewith.

7. The assembly of claim 6 wherein the connector means, the retainer means and the hub chamber are each dimensioned and configured to cooperate with each other to provide a stronger engagement force between the retainer means and the hub chamber than between the retainer means and the connector means.

8. The assembly of claim 6 wherein the clamping means comprise split segments of a ring and the ferrule slide is of cylindrical configuration.

9. A catheter assembly comprising:
  (a) a catheter having a hub within which is formed a hub chamber, and a catheter tube extending from the hub and terminating in a tube tip, the tube having a tube bore extending therethrough;
  (b) a needle assembly carried by the catheter and comprising a needle member in which is mounted a blunting member,
    (i) the needle member comprising a needle shaft having a needle bore extending therethrough, the needle shaft terminating at one end in a puncture tip and having an opposite, proximal end on which is carried a connector means,
    (ii) the blunting member comprising an elongate probe having a retainer means carried thereon, the probe being slidably mounted within the needle bore with the retainer means carried exteriorly of the needle bore and in engagement with the connector means, (iii) the needle member being axially movable relative to the blunting member, from a retracted condition of the blunting member, in which the probe is short of the puncture tip of the needle member, to an extended condition of the blunting member, in which the probe protrudes outwardly of, and thereby blunts, the puncture tip; the retainer means being force-fit within the hub chamber to hold the needle assembly in place within the catheter and so positioned that (1) the needle shaft is disposed within the tube bore with the puncture tip thereof extending outwardly of the tube tip, and (2) the needle member is accessible from exteriorly of the catheter at the hub; the retainer means and the connector means being dimensioned and configured to provide a lost motion connection between the needle member and the blunting member, whereby an initial stage of withdrawal of the needle member from the catheter moves the needle member relative to the blunting member to change the blunting member from its retracted condition to its extended condition, thereby blunting the puncture tip, and continued withdrawal of the needle member beyond the initial stage overcomes the force-fit between the retainer means and the hub chamber and extracts the needle assembly from the catheter.

10. The catheter assembly of claim 9 or claim 1 wherein the retainer means is in slidable engagement with the connector means.

11. A self-blunting needle assembly for use with a catheter having a hub within which is formed a hub chamber, and a catheter tube extending from the hub and terminating in a tube tip, the tube having a tube bore extending therethrough, the needle assembly comprising:

(a) a needle member in which is mounted a blunting member, (i) the needle member comprising a needle shaft having a needle bore extending therethrough, the needle shaft terminating at one end in a puncture tip and having an opposite, proximal end on which is carried a connector means, (ii) the blunting member comprising an elongate probe having a retainer means carried thereon, the probe being slidably mounted within the needle bore with the retainer means carried exteriorly of the needle bore and in engagement with the connector means, (iii) the needle member being axially movable relative to the blunting member, from a retracted condition of the blunting member, in which the probe is short of the puncture tip, to an extended condition of the blunting member, in which the probe protrudes outwardly of, and thereby blunts, the puncture tip of the needle member; the retainer means being dimensioned and configured to be force-fit within the hub chamber of a catheter to hold the needle assembly in place within such catheter and so positioned that (1) the needle shaft would be disposed within the tube bore of such catheter with the puncture tip thereof extending outwardly of the tube tip of such catheter, and (2) the needle member would be accessible from exteriorly of such catheter at the hub thereof; the retainer means and the connector means being dimensioned and configured to provide a lost motion connection between the needle member and the blunting member, whereby an initial stage of withdrawal of the needle member from such catheter moves the needle member relative to the blunting member to change the blunting member from its retracted condition to its extended condition, thereby blunting the needle, and continued withdrawal of the needle member beyond the initial stage overcomes the force-fit between the retainer means and the hub chamber of such catheter and extracts the needle assembly from such catheter.

12. The needle assembly of claim 11 or claim 2 wherein the retainer means is in slidable engagement with the connector means.

* * * * *